United States Patent [19]

Seamans et al.

[11] Patent Number: 4,490,386

[45] Date of Patent: Dec. 25, 1984

[54] PHOSPHATE SALTS OF 1-[2-[(1-ALKOXYCARBONYL-3-ARALKYL)-AMINO]-1-OXOALKYL]OCTAHYDRO-1H-INDOLE-2-CARBOXYLIC ACIDS, PREPARATION OF, AND MEDICAL COMPOSITIONS THEREOF

[75] Inventors: Ronald E. Seamans; Walter E. Behnke, both of Holland, Mich.

[73] Assignee: Warner-Lambert Company, Morris Plains, N.J.

[21] Appl. No.: 422,499

[22] Filed: Sep. 23, 1982

[51] Int. Cl.³ ................ A61K 31/405; C07D 209/18
[52] U.S. Cl. .................................... 424/274; 548/492
[58] Field of Search ............... 548/492; 424/274; 546/170

[56] References Cited

U.S. PATENT DOCUMENTS 3,391,146  7/1968  Godfrey .............................. 546/170
4,350,704  9/1982  Hoefle et al. ....................... 546/170

Primary Examiner—Glennon H. Hollrah
Assistant Examiner—D. B. Springer
Attorney, Agent, or Firm—Jerry F. Janssen

[57] ABSTRACT

Phosphate salts of the substituted acyl derivatives of octahydro-1H-indole-2-carboxylic acid are produced by treating a suitably substituted octahydro-1H-indole with phosphoric acid. The phosphate salts of the compounds and pharmaceutical compositions thereof are useful as antihypertensive agents.

3 Claims, No Drawings

PHOSPHATE SALTS OF 1-[2-[(1-ALKOXYCARBONYL-3-ARALKYL)-AMINO]-1-OXOALKYL]OCTAHYDRO-1H-INDOLE-2-CARBOXYLIC ACIDS, PREPARATION OF, AND MEDICAL COMPOSITIONS THEREOF

SUMMARY AND DETAILED DESCRIPTION

The invention relates to phosphate salts of substituted acyl derivatives of octahydro-1H-indole-2-carboxylic acid compounds having the formula

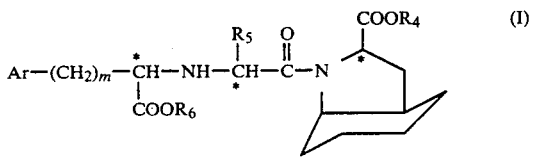

wherein $R_4$ and $R_6$ are hydrogen or lower alkyl, $R_5$ is hydrogen, lower alkyl or benzyl; Ar is phenyl or phenyl substituted with 1 or 2 substituents selected from the group consisting of fluorine, chlorine, bromine, lower alkyl, lower alkoxy, hydroxy or amino; and m is 0 to 3. The terms lower alkyl and lower alkoxy include groups having straight or branched chains and containing 1 to 4 carbon atoms.

Preferred compounds of the invention are phosphate salts of acylated octahydro-1H-indole-2-carboxylic acids having the formula

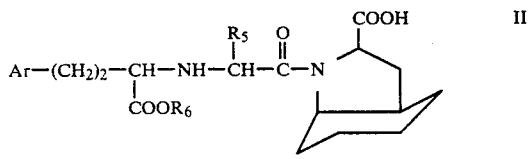

where $R_5$ is hydrogen or lower alkyl containing 1 to 3 carbon atoms; $R_6$ is hydrogen or lower alkyl containing 1 to 3 carbon atoms; and Ar is phenyl, and phenyl substituted in the para position by fluorine, chlorine, bromine, methyl, hydroxy, methoxy or amino.

Further preferred compounds of the invention are phosphate salts of acylated octahydro-1H-indole-2-carboxylic acids having the formula

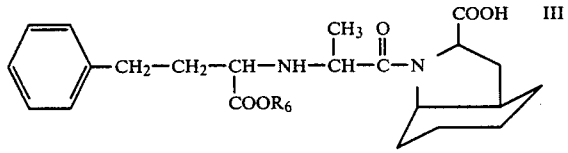

where $R_6$ is hydrogen, lower alkyl of 1 to 3 carbon atoms; and specifically the phosphate salts of the compounds designated 1-[2-[(1-carboxy-3-phenylpropyl)-amino]-1-oxopropyl]octahydro-1H-indole-2-carboxylic acid; 1-[2-[(1-carbomethoxy-3-phenylpropyl)amino]-1-oxopropyl]octahydro-1H-indole-2-carboxylic acid; and 1-[2-[(1-carboethoxy-3-phenylpropyl)amino]-1-oxopropyl]-octahydro-1H-indole-2-carboxylic acid.

The compounds of the invention have asymmetric carbon atoms. These carbon atoms are indicated by an asterisk in formula I. Additional asymmetric carbon atoms may be present in the lower alkyl groups. The compounds accordingly exist as optical isomers and disastereomers or as racemates and mixtures thereof. All of these are within the scope of the invention.

The compounds of the invention may exist in anhydrous form as well as in solvated, including hydrated, forms. In general, the hydrated forms and the solvated forms with pharmaceutically acceptable solvents are equivalent to the anhydrous or unsolvated form for the purposes of the invention.

The compounds of formula I may be prepared from octahydro-1H-indole-2-carboxylic acid by first protecting the carboxylic acid group, preferably as an ester, e.g., with a lower alkyl, benzyl or trimethylsilyl group. The protected carboxylic acid compound is coupled to an N-protected amino acid, e.g., glycine or L-alanine, protected on nitrogen with t-butyloxycarbonyl or benzyloxycarbonyl. The coupling is carried out by any of a variety of standard peptide coupling techniques as disclosed, for example, in "The Peptides. Analysis, Synthesis, Biology, Vol. 1 Major Methods of Peptide Bond Formation, Part A," ed. E. Gross, J. Meierhofer, Academic Press N.Y. (1979). An especially useful method involves the use of a dehydrating agent, such as dicyclohexylcarbodiimide alone or in the presence of reagents forming reactive esters, e.g., 1-hydroxybenzotriazole, in suitable aprotic solvents such as dimethylformamide, acetonitrile, tetrahydrofuran or chlorinated hydrocarbons. This gives the intermediate N-protected-(2-aminoacyl)-octahydro-1H-indole-2-carboxylic acid esters. These may then be either partially or totally deblocked depending on the protecting groups chosen, using anhydrous acids, e.g., hydrochloric acid in acetic acid or trifluoroacetic acid in dichloromethane or hydrogen gas and a catalyst to give the intermediate dipeptide either in free form or protected as an ester.

The compounds of formula I may then be prepared by reacting the intermediate dipeptide or its ester derivative with α-keto-4-substituted phenylbutyric acid or its lower alkyl ester derivatives under dehydrating and reducing conditions. Preferred dehydrating agents include molecular sieves in aprotic solvents and preferred reducing agents include sodium cyanoborohydride or hydrogen gas with a catalyst.

Alternatively, the dipeptide or its ester derivative may be reacted with an α-halo-4-substituted phenylbutyric acid or its ester in the presence of a suitable basic reagent, such as triethylamine or alkali carbonates or bicarbonates, in a solvent, to give the compounds of the invention of formula I. Ester protected products may be hydrolyzed under basic or acidic reaction conditions to free acid derivatives, or, in the case of benzyl esters, catalytic hydrogenolysis may be preferred.

Alternately, compounds of formula I may be prepared in a different manner. This consists of applying either of the two methods described above for the attachment of the 2-(4-phenylbutyric acid) moiety to the protected dipeptide, first to glycine or L-alanine, protected as an ester, to give N-[2-(4-phenylbutyric acid)]-substituted glycine or L-alanine derivative.

After selective deblocking of the acid moiety on the glycine or alanine portion of the product, the resulting monoacid may be coupled, either directly or subsequent to suitable blocking of the amino group, via standard peptide coupling procedures to the octahydro-1H-indole-2-carboxylic acid ester. Selective or complete removal of the ester groups and any amine protecting groups yield the compounds of formula I.

The products are obtained typically as a mixture of diastereomers which can be separated by standard methods of fractional crystallization or chromatography.

The pharmaceutically acceptable acid addition salts of the compounds of formula I may be prepared by conventional reactions with equivalent amounts of organic or inorganic acids. As exemplary, but not limiting, of pharmaceutically acceptable acid salts are the salts of hydrochloric, sulfuric, acetic, fumaric, malic, maleic and citric acids.

The phosphate salt of the present invention of the compounds of formula I offers a number of unexpected advantages over the salts set forth above.

As an example, in contrast to the hydrochloride salt, the phosphate salt of (2α, 3aβ, 7aβ)-1-[2-[(1-carboethoxy-3-phenylpropyl)amino]-1-oxopropyl]-octahydro-1H-indole-2-carboxylic acid (S,S,S-isomer) is a crystalline, relatively nonhygroscopic solid whereas the hydrochloride is obtained only as an amorphous, freeze-dried, hygroscopic compound. Manufacturing advantages are apparent in circumventing the lengthy freeze-drying process.

The phosphate salt is easily purified to a higher degree than the hydrochloride salt. The phosphate salt is a white, dense solid as opposed to the hydrochloride salt which is a pink to a rose colored solid. The phosphate salt is soluble in water to give a clear, colorless solution whereas the hydrochloride salt gives a hazy, deep red colored solution in water.

A dense crystalline phosphate salt has advantages over the hydrochloride in the ease of formulation.

The phosphate salts of this invention of the compounds of formula I intervene in the renin→angiotensin I→angiotensin II sequence by inhibiting angiotensin I converting enzyme and reducing or eliminating the formation of the pressor substance angiotensin II, and therefore are useful in reducing or relieving hypertension. Thus by the administration of a composition containing one or a combination of compounds of formula I as a phosphate salt thereof, hypertension in the species of mammal suffering therefrom is alleviated. The biological activity of the compounds of formula I and the dosages to be administered is disclosed in U.S. Pat. No. 4,350,704, issued Sept. 21, 1982.

The present invention is illustrated by the following examples.

EXAMPLE 1

(2α, 3aβ, 7aβ)-1-[2-[(1-Carboethoxy-3-phenylpropyl)amino]-1-oxopropyl]octahydro-1H-indole-2-carboxylic Acid Hydrochloride, (S,S,S-isomer)

A solution of 1.23 g of the S,S isomer of ethyl α-[(1-carboxyethyl)amino]benzenebutanoate hydrochloride, 0.92 g of t-butyl (1)-octahydro-1H-indole-2-carboxylate, 0.53 g of 1-hydroxybenzotriazole, monohydrate, and 0.54 ml of triethylamine in 15 ml of N,N-dimethylformamide is cooled in ice and treated dropwise with a solution of 0.8 g of N,N'-dicyclohexylcarbodiimide in 2 ml of N,N-dimethylformamide. After stirring for 1 hour at 0° C., the cooling is removed and the mixture allowed to stir at room temperature overnight.

The mixture is filtered to remove dicyclohexylurea, and the N,N-dimethylformamide removed by distillation under high vacuum. The residue is taken up in ethyl acetate, washed two times with saturated sodium bicarbonate solution and then with saturated sodium chloride solution. Drying over magnesium sulfate and removal of the solvent under reduced pressure leaves an oil. This is taken up in ether, filtered, and the ether is removed under reduced pressure leaving 1.9 g of the crude t-butyl ester of the product as an oil.

A solution of 0.63 g of this t-butyl ester in 6 ml of dichloromethane is saturated with hydrogen chloride gas and allowed to stir at room temperature overnight. The solvent is removed under reduced pressure, more dichloromethane is added, and the solvent removed again. The residue is taken up in dichloromethane, treated with charcoal, and filtered. Removal of the solvent under reduced pressure gives a foam. This is triturated with ether and collected giving 0.35 g (58% yield) of the product, $[\alpha]_D^{23} = -29.7°$ (1.01%, 1:1 methanol/1N hydrochloric acid).

The intermediate S,S-isomer of ethyl α-[(1-carboxyethyl)amino]benzenebutanoate hydrochloride used in this preparation may be prepared in the following manner. A solution of 2.0 g of t-butyl L-alanine and 3.78 g of ethyl 2-bromo-4-phenylbutanoate in 25 ml of dimethylformamide is treated with 1.8 ml of triethylamine and the solution is heated at 70° C. for 18 hours. The solvent is removed at reduced pressure and the residue is mixed with water and extracted with ethyl ether. The organic layer is washed with water and dried over magnesium sulfate. Concentration of the solvent at reduced pressure gives the oily t-butyl ester of the intermediate which is found to be sufficiently pure by gas liquid chromatography for further use.

A solution of 143.7 g of this t-butyl ester in 630 ml of trifluoroacetic acid is stirred at room temperature for one hour. The solvent is removed at reduced pressure and the residue is dissolved in ethyl ether and again evaporated. This operation is repeated. Then the ether solution is treated dropwise with a solution of hydrogen chloride gas in ethyl ether until precipitation ceases. The solid is collected by filtration and is a mixture of diastereoisomers, mp 153°–165° C., $[\alpha]_D^{23} = +3.6°$ (c = 1, methanol).

In order to separate the preferred S,S isomer, a suspension of 10.0 g of the mixture in 200 ml of methylene chloride is stirred at room temperature for five minutes and filtered; the solid material, mp 202°–204° C. (dec.), $[\alpha]_D^{23} = -29.3°$ (c = 1, methanol) is the less preferred diastereoisomer having the R,S configuration (S referring to the portion derived from L-alanine). The preferred S,S-diastereoisomer can be recovered from the filtrate after concentration and trituration of the residue with ether. It has mp 137°–139° C., $[\alpha]_D^{23} = +31.3°$ (c = 1, methanol).

Resolution of octahydro-1H-indole-2-carboxylic acid

A solution of 20.0 g of racemic (2α, 3aβ, 7aβ)-octahydro-1H-indole-2-carboxylic acid in 200 ml of water is cooled in an ice bath and treated dropwise during 1.5 hours simultaneously but separately with 14.4 ml of benzoyl chloride and 120 ml of 2N sodium hydroxide solution, keeping the pH between 6 and 8. The solution is stirred for an additional 30 minutes and the pH is adjusted to 1.8 with 1N hydrochloric acid. Racemic N-benzoyl-(2α, 3aβ, 7aβ)-octahydro-1H-indole-2-carboxylic acid precipitates and is collected by filtration. Recrystallization from aqueous ethanol gives pure product, mp 191°–193° C.

This compound, 87.75 g, is added to a solution of 38.9 g, of (1)-α-phenylethylamine in 700 ml of methanol to form a solution. This is diluted with 1250 ml of ethyl acetate and seeded with a crystal of the resolved salt.

The mixture begins to precipitate the desired salt. After standing 18 hours at 5° C., the salt, collected by filtration, has mp 212°-215° C.(dec.) and $[\alpha]_D^{23} = -49.4°$ (C=1, methanol). Recrystallization from a 2:1 mixture of ethyl acetate and methanol gives product with the same mp and rotation.

The levorotatory salt, 48.2 g, is suspended in a mixture of 884 ml of water and 353 ml of methanol and acidified with dilute hydrochloric acid to pH 2. After 15 minutes, the initial solid dissolves and a new solid separates. Water, 430 ml, is added and the (1)-N-benzoyl-(2α, 3aβ, 7aβ)-octahydro-1H-indole-2-carboxylic acid is collected by filtration, mp 169°-171° C., $[\alpha]_D^{23} = -51.4°$ (C=1, methanol).

A suspension of the (1)-benzoate in 200 ml of 6N hydrochloric acid is heated at reflux for 4 hours. The resulting solution is diluted with 100 ml of water and cooled. Filtration removes precipitated benzoic acid. The filtrate is extracted with chloroform and the pH of the aqueous layer is adjusted to 6.5 with dilute sodium hydroxide solution. Concentration of this to dryness gives a solid which is ground and extracted with anhydrous ethanol. Concentration of the ethanol extract gives (1)-(2α, 3aβ, 7aβ)-octahydro-1H-indole-2-carboxylic acid which may be purified by passing it through an ion exchange resin in the acid form and eluting with 2N ammonium hydroxide, isolating the solid and recrystallizing this from anhydrous ethanol. The pure (1)-amino acid has mp 265°-266° C. (dec.), $[\alpha]_D^{23} = -48.5°$ (C=1, methanol).

The intermediate t-butyl (1)-octahydro-1H-indole-2-carboxylate used in this preparation is prepared as follows. A solution of 14.23 g of (1)-octahydro-1H-indole-2-carboxylic acid in 150 ml of dioxane contained in a pressure vessel is treated with 15 ml of concentrated sulfuric acid and 84 g of isobutylene and kept at 20° C. for 20 hours with stirring. The mixture is then poured into ice water containing 45 ml of 50% sodium hydroxide solution and the mixture is extracted three times with ether. The ether is washed with water, then saturated sodium chloride solution. Drying over magnesium sulfate and removal of the ether under reduced pressure gives 14.4 g of the desired t-butyl ester as an oil, $[\alpha]_D^{23} = -27.6°$ (1.1% in methanol).

EXAMPLE 2

(2α, 3aβ, 7aβ)-1-[2-[(1-carboethoxy-3-phenylpropyl)amino]-1-oxopropyl]octahydro-1H-indole-2-carboxylic Acid Phosphate (1:1), (S,S,S-isomer)

(2α, 3aβ, 7aβ)-1-[2-[(1-Carboethoxy-3-phenylpropyl)amino]-1-oxopropyl]octahydro-1H-indole-2-carboxylic acid hydrochloride, (S,S,S-isomer), prepared by the process of Example 1, 5 g (0.0107 mole) was dissolved in 40 ml of tetrahydrofuran. The colored solution was treated with 1.08 g (1.50 ml., 0.0107 mole) of triethylamine whereupon a white precipitate of triethylamine hydrochloride formed. The slurry was chilled for 10 to 15 minutes, then the solid filtered off and washed with tetrahydrofuran (10 ml.). The filtrate was treated with 1.23 g (0.0107 mole) of 85% phosphoric acid, seeded and cooled overnight whereupon crystalline material precipitated from solution. The product was recrystalized from tetrahydrofuran (75 ml) containing 0.5 g of 85% phosphoric acid to give 2.9 g of white, crystalline (2α, 3aβ, 7aβ)-1-[2-[(1-carboethoxy-3-phenylpropyl)amino]-1-oxopropyl]octahydro-1H-indole-2-carboxylic acid phosphate (1:1), (S,S,S-isomer), $[\alpha]_D^{25} = -23.7°$ (50% MeOH:1NHCl), mp 110°-115° C.

EXAMPLE 3

(2α, 3aβ, 7aβ)-1-[2-[(1-Carboethoxy-3-phenylpropyl)amino]-1-oxopropyl]octahydro-1H-indole-2-carboxylic Acid Phosphate (1:1), (S,S,S-isomer)

A 1000 g (2.14 moles) quantity of (2α, 3aβ, 7aβ)-1-[2-[(1-carboethoxy-3-phenylpropyl)amino]-1-oxopropyl]octahydro-1H-indole-2-carboxylic acid hydrochloride,(S,S,S-isomer, prepared by the process of Example was added with stirring to 6.0 L of tetrahydrofuran at room temperature. The solution was treated with 216.7 g (2.14 moles) of triethylamine, immediately precipitating a white solid. The slurry was stirred and cooled in an ice bath for 30 minutes with the temperature of the mixture dropping to 12° C. The solid was filtered off on a Buchner funnel and washed with 1.0 L of room temperature tetrahydrofuran.

The filtrate was treated with 296.2 g (2.57 moles) of 85% phosphoric acid. Seed crystals were added and the solution cooled overnight to allow full precipitation to take place.

The precipitated product was filtered on a Buchner funnel with fresh tetrahydrofuran used as a wash. This solid was dried in vacuo at 40° C. to give 1075 g of crude phosphate salt which was analyzed by VPC as containing 10-12% tetrahydrofuran.

The crude phosphate salt (1075 g) was dissolved in 4.3 L of boiling absolute ethanol. This heating time was kept as short as possible to prevent the formation of an unwanted cyclic by-product. The hot solution was filtered into a container chilled by ice water. A 1.075 L quantity of hot absolute ethanol was used as a wash. The combined filtrates were seeded and chilled overnight to allow precipitation to occur. Hexane (5.375 L) was added to further precipitate the product. After several hours of crystallization, the product was collected and washed several times with fresh hexane. The phosphate salt was dried *in vacuo* (5-10 mm) at a temperature of 40° C. for four days. There was obtained 835 g of phosphate salt.

VPC 1.13% EtOH, 0.39% THF

HPLC ≃97.9% (≃2.10% cyclic by-product obtained).

EXAMPLE 4

1000 tablets each containing 100 mg of (2α, 3aβ, 7aβ)-1-[2-[(1-carboethoxy-3-phenylpropyl)amino]-1-oxopropyl]octahydro-1H-indole-2-carboxylic acid phosphate (1:1), (S,S,S-isomer) are produced from the following ingredients: (2α, 3aβ, 7aβ)-1-[2-[(1-Carboethoxy-3-phenylpropyl)amino]-1-oxopropyl]octahydro-1H-indole-2-carboxylic acid phosphate (1:1), (S,S,S-isomer): 100 g Corn Starch: 50 g Gelatin: 7.5 g Avicel (microcrystalline cellulose): 25 g Magnesium Stearate: 2.5 g The (2α, 3aβ, 7aβ)-1-[2-[(1-carboethoxy-3-phenylpropyl)amino]-1-oxopropyl]octahydro-1H-indole-2-carboxylic acid phosphate (1:1), (S,S,S-isomer) and corn starch are admixed with an aqueous solution of the gelatin. The mixture is dried and ground to a fine powder. The Avicel and then the magnesium stearate are admixed with the granulation. This is then compressed in a tablet press to form 1000 tablets each containing 100 mg of active ingredients.

The phosphate salt obtained can also be designated [2S-[1[R*(R*)], 2α, 3aβ, 7aβ]]-1-[2-[[1-(ethoxycarbonyl)-3-phenylpropyl]amino]-1-oxopropyl]octahydro-1H-indole-2-carboxylic acid, phosphate, (salt) (1:1).

We claim:

1. The crystalline phosphate salt of the compound which is 1-[2-[(1-carboethoxy-3-phenylpropyl)amino]-1-oxopropyl]octahydro-1H-indole-2-carboxylic acid.

2. A process for the production of a crystalline phosphate salt of the substituted acyl derivative of octahydro-1H-indole-2-carboxylic acid having the formula

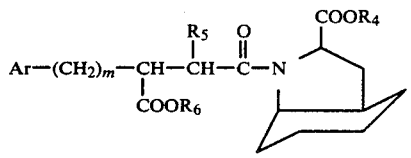

wherein $R_4$ is hydrogen or lower alkyl; $R_5$ is hydrogen, lower alkyl or benzyl; $R_6$ is hydrogen or lower alkyl; Ar is phenyl or phenyl substituted with 1 or 2 substituents selected from the group consisting of fluorine, chlorine, bromine, lower alkyl, lower alkoxy, hydroxy or amino; and m is 0 to 3; wherein lower alkyl and lower alkoxy contain 1 to 4 straight or branched carbon atoms;

said process comprising the steps (a) treating the suitably substituted acyl derivative of octahydro-1H-indole-2-carboxylic acid addition salt, wherein the acid addition salt is other than the phosphate salt, with a base in a suitable solvent, (b) filtering the resulting slurry to remove precipitated material, and (c) treating the filtrate with phosphoric acid and collecting the precipitated phosphate salt.

3. A pharmaceutical composition comprising the crystalline phosphate salt of 1-(2-((1-carboethoxy-3-phenylpropyl)amino)-1-oxopropyl)octahydro-1H-indole-2-carboxylic acid and a pharmaceutically acceptable carrier.

* * * * *